United States Patent

Mitchell et al.

[11] Patent Number: 5,283,262
[45] Date of Patent: Feb. 1, 1994

[54] PHENETHANOLAMINE DERIVATIVES

[75] Inventors: William L. Mitchell, London; Ian F. Skidmore, Welwyn; Lawrence H. C. Lunts, Broxbourne; Harry Finch, Letchworth; Alan Naylor, Royston; David Hartley, Knebworth, all of England

[73] Assignee: Glaxo Group Limited, London, England

[21] Appl. No.: 812,757

[22] Filed: Dec. 23, 1991

Related U.S. Application Data

[60] Division of Ser. No. 622,506, Dec. 5, 1990, Pat. No. 5,109,023, which is a continuation of Ser. No. 270,945, Nov. 14, 1988, Pat. No. 4,997,986.

[30] Foreign Application Priority Data

Nov. 13, 1987 [GB] United Kingdom ............... 8726586
Sep. 9, 1988 [GB] United Kingdom ............... 8821179

[51] Int. Cl.$^5$ ............................................ A61K 31/135
[52] U.S. Cl. ......................... 514/651; 514/654; 514/886; 514/887; 514/913; 514/925; 514/927; 564/363; 564/364
[58] Field of Search ............ 564/364, 89, 90, 161, 564/363; 514/651, 886, 654, 887, 913

[56] References Cited

U.S. PATENT DOCUMENTS 4,730,008  3/1988  Skidmore et al. .................. 514/605

FOREIGN PATENT DOCUMENTS 1330188   9/1973  United Kingdom .
2140800  12/1984  United Kingdom .
2159151  11/1985  United Kingdom .
2165542   4/1986  United Kingdom .
2182658   5/1987  United Kingdom .

*Primary Examiner*—Glennon H. Hollrah
*Assistant Examiner*—Shailendra Kumar
*Attorney, Agent, or Firm*—Morgan & Finnegan

[57] ABSTRACT

The invention provides compounds of the general formula (I)

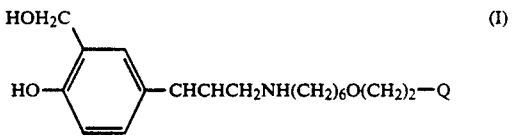

or a physiologically acceptable salt or solvate thereof, wherein Q represents a 1- or 2-naphthalenyl group.

The compounds have a stimulant action at $\beta_2$-adrenoreceptors and may be used in the treatment of diseases associated with reversible airways obstruction such as asthma and chronic bronchitis.

3 Claims, No Drawings

PHENETHANOLAMINE DERIVATIVES

This application is a divisional of copending application Ser. No. 07/622,506 filed on Dec. 5, 1990, now U.S. Pat. No. 5,109,023; which is a continuation of Ser. No. 07/270,945 filed Nov. 14, 1988, now U.S. Pat. No. 4,997,986.

This invention relates to phenethanolamine derivatives having a stimulant action at $\beta_2$-adrenoreceptors, to processes for their preparation, to pharmaceutical compositions containing them and to their use in medicine.

Phenethanolamine derivatives of the general formula

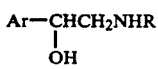

in which Ar represents groupings of the type described hereinafter, and R represents inter alia an alkyl, aralkyl, aryloxyalkyl or an optionally substituted phenylalkyloxyalkyl group have previously been described as bronchodilators having stimulant activity at $\beta$-adrenoreceptors.

Thus, for example, British Patent Specification No. 1200886 describes phenethanolamine compounds of the general structure

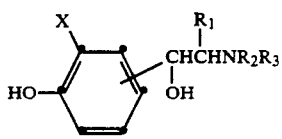

in which X represents inter alia a hydroxy$C_{1-6}$alkyl group; $R_1$ represents a hydrogen atom or an optionally branched $C_{1-6}$alkyl group; $R_2$ represents inter alia a hydrogen atom; and $R_3$ represents a hydrogen atom or an optionally branched $C_{1-6}$ alkyl group, optionally substituted by hydroxyl or amino groups or heterocyclic rings, or $R_3$ represents a cycloalkyl, aralkyl or aryloxyalkyl group, optionally substituted by one or more alkoxy or hydroxyl groups.

UK Patent Specification No. 2140800 describes phenethanolamine compounds of the general structure

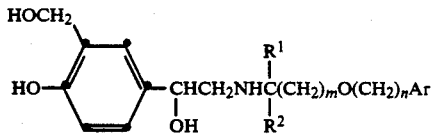

in which $R^1$ and $R^2$ each represent hydrogen or $C_{1-3}$ alkyl; m is an integer from 2 to 8; n is an integer from 1 to 7; and Ar represents an optionally substituted phenyl ring.

We have now found a novel group of phenethanolamine derivatives which differ in structure from those described previously (for example, British and UK Patent Specification Nos. 1200886 and 2140800), and have a desirable and potentially useful profile of activity.

Thus the present invention provides compounds of the general formula (I)

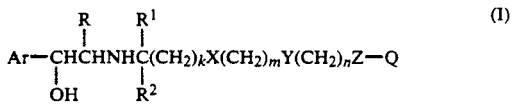

and physiologically acceptable salts and solvents (e.g. hydrates) thereof, wherein Ar represents the group

(where $Q^1$ represents a straight or branched $C_{1-3}$ alkylene group),

(where $Q^2$ represents a group $R^3CO—$, $R^3NHCO—$, $R^3R^4NSO_2—$ or $R^5SO_2—$, where $R^3$ and $R^4$ each represent a hydrogen atom or a $C_{1-3}$ alkyl group, and $R^5$ represents a $C_{1-3}$ alkyl group),

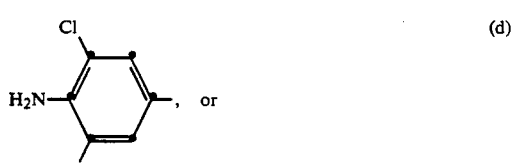

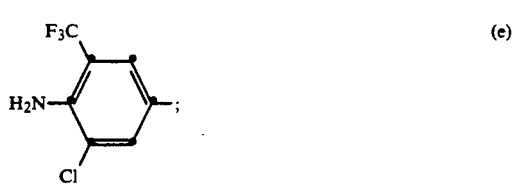

R represents a hydrogen atom or a $C_{1-3}$ alkyl group;
$R^1$ and $R^2$ each independently represent a hydrogen atom or a methyl or ethyl group; and
k represents an integer from 1 to 8;
m represents zero or an integer from 2 to 7, and;
n represents an integer from 1 to 7 with the proviso that the sum total of k, m and n is 4 to 12;
X represents an oxygen or sulphur atom, and;
Y and Z each represent a bond, or an oxygen or sulphur atom with the proviso that when Y is a bond m is zero, or when Y represents an oxygen or sulphur atom m is an integer from 2 to 7, or when Y and Z each independently represent an oxygen or sulphur atom then n is an integer from 2 to 7;

Q represents a naphthalenyl group which may optionally be substituted by one or two groups selected from $C_{1-4}$ alkyl, $C_{1-4}$ alkoxy, hydroxy and halogen.

It will be appreciated that the compounds of general formula (I) possess one or more asymmetric carbon atoms. The compounds according to the invention thus include all enantiomers, diastereoisomers and mixtures thereof, including racemates. Compounds in which the carbon atom in the —CH(OH)— group is in the R configuration are preferred.

In the general formula (I), the chain —$(CH_2)_k$— may be for example a bond, —$CH_2$—, —$(CH_2)_2$—, —$(CH_2)_3$—, —$(CH_2)_4$—, —$(CH_2)_5$—, —$(CH_2)_6$— or —$(CH_2)_7$—. The chains —$(CH_2)_m$— and —$(CH_2)_n$— may be for example —$(CH_2)_2$—, —$(CH_2)_3$—, —$(CH_2)_4$—, —$(CH_2)_5$— or —$(CH_2)_6$— or the chain —$(CH_2)_m$— may be a bond.

Preferably the total number of carbon atoms in the chains —$(CH_2)_k$—, —$(CH_2)_m$— and —$(CH_2)_n$— is 6 to 12 inclusive. Compounds wherein the sum total of carbon atoms in the chains —$(CH_2)_k$—, —$(CH_2)_m$ and —$(CH_2)_n$— is 6, 7, 8, 9, 10 or 11 are particularly preferred.

Examples of compounds of general formula (I) are those wherein X represents an oxygen or sulphur atom and Y and Z each represent a bond. Further examples are those wherein X represents an oxygen or sulphur atom, Y represents a bond and Z represents an oxygen or sulphur atom. Still further examples of compounds of general formula (I) are those wherein X, Y and Z each represent oxygen or sulphur atoms.

A preferred group of compounds of general formula (I) are those in which X is an oxygen atom. Within this group of compounds Y preferably represents a bond or an oxygen atom and Z represents a bond or an oxygen or sulphur atom.

Preferred compounds from within this group are those wherein X is an oxygen atom, Y is a bond and Z is a bond, or X is an oxygen atom, Y is a bond and Z is an oxygen or sulphur atom.

In the compounds of formula (I) R may be, for example, a methyl, ethyl, propyl or isopropyl group. R, $R^1$ and $R^2$ are each preferably a hydrogen atom or a methyl group.

A preferred group of compounds are those in which R represents a hydrogen atom.

Another preferred group of compounds are those wherein $R^1$ and $R^2$ are both hydrogen atoms, or $R^1$ is a hydrogen atom and $R^2$ is a $C_{1-3}$ alkyl group, particularly a methyl group, or $R^1$ is a methyl group and $R^2$ is a methyl group.

In the compounds of formula (I), $Q^1$ may be, for example, —$CH_2$—, —$CH(CH_3)$—, —$(CH_2)_2$— or —$(CH_2)_3$—. A preferred group of compounds are those in which $Q^1$ represents —$CH_2$—.

$Q^2$ may represent for example HCO—, $CH_3$CO—, $H_2$NCO—, $(CH_3)_2NSO_2$— or $CH_3SO_2$—.

$Q^2$ preferably represents HCO— or, more particularly, $CH_3SO_2$—.

The group Q is attached to the rest of the molecule through any available position on the naphthalenyl moiety. Any substituent(s) in the group Q may be attached to either the same or different rings of the naphthalenyl moiety. When the group Q is substituted by one or two halogen atoms, these may be chlorine, fluorine or bromine.

A preferred group of compounds of general formula (I) are those wherein Q is an unsubstituted naphthalenyl moiety attached to the remainder of the molecule at the 1- or 2-position.

A further group of preferred compounds of formula (I) are those in which the group Q is substituted by a single substituent, for example, a methoxy group.

In one preferred group of compounds of general formula (I) Ar represents group (a) wherein $Q^1$ represents —$CH_2$—, or group (b) wherein $Q^2$ represents $CH_3SO_2$—, or group (c) or group (d); R represents a hydrogen atom; $R^1$ represents a hydrogen atom or a methyl group; $R^2$ represents a hydrogen atom; X represents an oxygen atom; Y represents a bond; Z represents a bond or an oxygen or sulphur atom; and k is 5, m is zero and n is an integer from 1 to 4.

Preferred compounds according to the invention are
4-hydroxy-$\alpha^1$-[[[6-[2-(2-naphthalenyl)ethoxy]hexyl]amino]methyl]-1,3-benzenedimethanol,
4-amino-3,5-dichloro-$\alpha$-[[[6-[3-(6-methoxy-2-naphthalenyl)propoxy]hexyl]amino]methyl]benzenemethanol,
5-[1-hydroxy-2-[[6-[(2-naphthalenyl)ethoxy]hexyl]amino]ethyl]-1,3-benzenediol,
N-[2-hydroxy-5-[1-hydroxy-2-[[6-[4-[(2-naphthalenyl)oxy]butoxy]hexyl]amino]ethyl]phenyl]methanesulphonamide, and
4-hydroxy-$\alpha^1$-[[[6-[2-(1-naphthalenyl)ethoxy]hexyl]amino]methyl]-1,3-benzenedimethanol, and their physiologically acceptable salts and solvates.

Suitable physiologically acceptable salts of the compounds of general formula (I) include acid addition salts derived from inorganic and organic acids, such as hydrochlorides, hydrobromides, sulphatres, phosphates, maleates, tartrates, citrates, benzoates, 4-methoxybenzoates, 2- or 4-hydroxybenzoates, 4-chlorobenzoates, benzenesulphonates, p-toluenesulphonates, naphthalenesulphonates, methanesulphonates, sulphamates, ascorbates, salicylates, acetates, diphenylacetates, triphenylacetates, adipates, fumarates, succinates, lactates, glutarates, gluconates, tricarballylates, hydroxynaphthalenecarboxylates e.g. 1-hydroxy- or 3-hydroxy-2-naphthalenecarboxylates, or oleates. The compounds may also form salts with suitable bases where appropriate. Examples of such salts are alkali metal (e.g. sodium and potassium) and alkaline earth metal (e.g. calcium or magnesium) salts, and salts with organic bases (e.g. triethylamine).

The compounds according to the invention have a stimulant action at $\beta_2$-adrenoreceptors, which furthermore is of a particularly advantageous profile. The stimulant action was demonstrated in the isolated trachea of the guinea-pig, where compounds were shown to cause relaxation of contractions induced by $PGF_{2\alpha}$ or electrical stimulation. A prolonged duration of action has also been observed.

The compounds according to the invention may be used in the treatment of diseases associated with reversible airways obstruction such as asthma and chronic bronchitis.

The compounds according to the invention are also indicated as useful for the treatment of inflammatory and allergic skin diseases, congestive heart failure, depression, premature labour, glaucoma, and in the treatment of conditions in which there is an advantage in lowering gastric acidity, particularly in gastric and peptic ulceration.

The invention accordingly further provides compounds of formula (I) and their physiologically acceptable salts and solvates for use in the therapy or prophylaxis of diseases associated with reversible airways obstruction in human or animal subjects.

The compounds according to the invention may be formulated for administration in any convenient way. The invention therefore includes within its scope pharmaceutical compositions comprising at least one compound of formula (I) or a physiologically acceptable salt or solvate thereof formulated for use in human or veterinary medicine. Such compositions may be presented for use with physiologically acceptable carriers or excipients, optionally with supplementary medicinal agents.

The compounds may be formulated in a form suitable for administration by inhalation or insufflation, or for oral, buccal, parenteral, topical (including nasal) or rectal administration. Administration by inhalation or insufflation is preferred.

For administration by inhalation the compounds according to the invention are conveniently delivered in the form of an aerosol spray presentation from pressurised packs, with the use of a suitable propellant, such as dichlorodifluoromethane, trichlorofluoromethane, dichlorotetrafluoroethane, carbon dioxide or other suitable gas, or from a nebuliser. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in for example capsules or cartridges of e.g. gelatin, or blister packs from which the powder may be administered with the aid of an inhaler or insufflator.

For oral administration, the pharmaceutical composition may take the form of, for example, tablets, capsules, powders, solutions, syrups or suspensions prepared by conventional means with acceptable excipients.

For buccal administration the composition may take the form of tablets, drops or lozenges formulated in conventional manner.

The compounds of the invention may be formulated for parenteral administration by bolus injection or continuous infusion. Formulations for injection may be presented in unit dosage form in ampoules, or in multi-dose containers with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution with a suitable vehicle, e.g. sterile pyrogen-free water, before use.

For topical administration the pharmaceutical composition may take the form of ointments, lotions or creams formulated in a conventional manner, with for example an aqueous or oily base, generally with the addition of suitable thickening agents and/or solvents. For nasal application, the composition may take the form of a spray, formulated for example as an aqueous solution or suspension or as an aerosol with the use of a suitable propellant.

The compounds of the invention may also be formulated in rectal compositions such as suppositories or retention enemas, e.g. containing conventional suppository bases such as cocoa butter or other glyceride.

Where pharmaceutical compositions are described above for oral, buccal, rectal or topical administration, these may be presented in a conventional manner associated with controlled release forms.

A proposed daily dosage of active compound for the treatment of man is 0.005 mg to 100 mg, which may be conveniently administered in one or two doses. The precise dose employed will of course depend on the age and condition of the patient and on the route of administration. Thus a suitable dose for administration by inhalation is 0.005 mg to 20 mg, for oral administration is 0.02 mg to 100 mg, and for parenteral administration is 0.01 mg to 2 mg for administration by bolus injection and 0.01 mg to 25 mg for administration by infusion.

The compounds according to the invention may be prepared by a number of processes. In the following description, Ar, k, m, n, X, Y, Z, Q, R, $R^1$ and $R^2$ are as defined for general formula (I) unless otherwise specified. In the preparation of both intermediates and end-products the final step in the reaction may be the removal of a protecting group. Suitable protecting groups and their removal are described in general process (3) below.

In one general process (1), a compound of general formula (I) may be prepared by alkylation. Conventional alkylation procedures may be used.

Thus, for example, in one process (a), a compound of general formula (I) in which $R^1$ is a hydrogen atom may be prepared by alkylation of an amine of general formula (II)

(wherein $R^6$ is a hydrogen atom or a protecting group and R' is a hydrogen atom) followed by removal of any protecting group where present.

The alkylation (a) may be effected using an alkylating agent of general formula (III):

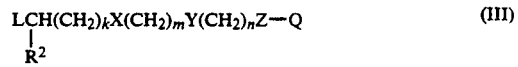

(wherein L is a leaving group, for example a halogen atom such as chlorine, bromine or iodine, or a hydrocarbylsulphonyloxy group such as methanesulphonyloxy or p-toluenesulphonyloxy).

The alkylation is preferably effected in the presence of a suitable acid scavenger, for example, inorganic bases such as sodium or potassium carbonate, organic bases such as triethylamine, diisopropylethylamine or pyridine, or alkylene oxides such as ethylene oxide or propylene oxide. The reaction is conveniently effected in a solvent such as acetonitrile or an ether e.g. tetrahydrofuran or dioxan, a ketone e.g. butanone or methyl isobutyl ketone, a substituted amide e.g. dimethylformamide or a chlorinated hydrocarbon e.g. chloroform, at a temperature between ambient and the reflux temperature of the solvent.

According to another example (b) of an alkylation process, a compound of general formula (I) in which $R^1$ represents a hydrogen atom may be prepared by alkylation of an amine of general formula (II), as previously defined except that R' is a hydrogen atom or a group convertible thereto under the reaction conditions, with a compound of general formula (IV):

$$R^2CO(CH_2)_kX(CH_2)_mY(CH_2)_nZ-Q \qquad (IV)$$

in the presence of a reducing agent, followed when necessary by removal of any protecting groups.

Examples of suitable R' groups convertible into a hydrogen atom are arylmethyl groups such as benzyl, α-methylbenzyl and benzhydryl.

Suitable reducing agents include hydrogen in the presence of a catalyst such as platinum, platinum oxide, palladium, palladium oxide, Raney nickel or rhodium, on a support such as charcoal, using an alcohol, e.g. ethanol or methanol, or an ester e.g. ethyl acetate, or an ether e.g. tetrahydrofuran, or water, as reaction solvent, or a mixture of solvents, e.g. a mixture of two or more of those just described, at normal or elevated temperature and pressure, for example from 20° to 100° C. and from 1 to 10 atmospheres.

Alternatively when one or both of $R^6$ and R' are hydrogen atoms, the reducing agent may be a hydride such as diborane or a metal hydride such as sodium borohydride, sodium cyanoborohydride or lithium aluminium hydride. Suitable solvents for the reaction with these reducing agents will depend on the particular hydride used, but will include alcohols such as methanol or ethanol, or ethers such as diethyl ether or tert-butyl methyl ether, or tetrahydrofuran.

When a compound of formula (II) where $R^6$ and R' are each hydrogen atoms is used, the intermediate imine of formula (V) may be formed:

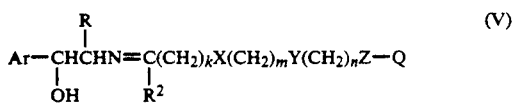

(V)

Reduction of the imine using the conditions described above, followed, where necessary, by removal of any protecting groups, gives compound of general formula (I).

In another general process (2) compounds of formula (I) may be prepared by reducing an intermediate of general formula (VI):

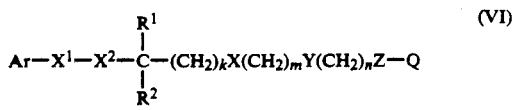

(VI)

wherein at least one of $X^1$ and $X^2$ represents a reducible group and the other(s) take the appropriate meaning as follows, which is $X^1$ is —CH(OH)— and $X^2$ is —CHRNR$^6$— (where $R^6$ represents a hydrogen atom or a protecting group), followed where necessary by removal of any protecting groups.

Suitable reducible groups include those wherein $X^1$ is a group >C=O and $X^2$ is a group —CHRNR$^8$— (wherein $R^8$ represents a group convertible to hydrogen by catalytic hydrogenation, for example an arylmethyl group such as benzyl, benzhydryl or α-methylbenzyl).

The reduction may be effected using reducing agents conveniently employed for the reduction of ketones or protected amines.

Thus, for example, when $X^1$ in general formula (VI) represents a >C=O group this may be reduced to a —CH(OH)— group using hydrogen in the presence of a catalyst such as platinum, platinum oxide, palladium, palladium oxide, Raney nickel or rhodium, on a support such as charcoal, using an alcohol e.g. ethanol, an ester e.g. ethyl acetate, an ether e.g. tetrahydrofuran, or water, as reaction solvent, or a mixture of solvents, e.g. a mixture of two or more of those just described, at normal or elevated temperature and pressure, for example from 20° to 100° C. and from 1 to 10 atmospheres. Alternatively, the reducing agent may be, for example, a hydride such as diborane or a metal hydride such as lithium aluminium hydride, sodium bis(2-methoxyethoxy) aluminium hydride, sodium borohydride or aluminium hydride. The reaction may be effected in an appropriate solvent, such as an alcohol e.g. methanol or ethanol, or an ether such as tetrahydrofuran, or a halogenated hydrocarbon such as dichloromethane.

When $X^2$ in general formula (VI) represents a —CHRNR$^8$ group this may be reduced to a —CHRNH— group using hydrogen in the presence of a catalyst as described above.

Where it is desired to use a protected intermediate of general formula (VI) it is particularly convenient to use a protecting group $R^6$ which is capable of being removed under the reducing conditions, for example hydrogen and a catalyst, thus avoiding the need for a separate deprotection step. Suitable protecting groups of this type include arylmethyl groups such as benzyl, benzyhydryl and α-methylbenzyl.

In the above reduction process, and also in the preparation of intermediates, care must be taken when using a hydride reducing agent and end-products are required in which $Q^2$ represents the group $R^3CO—$.

In a further process (3) compounds of formula (I) may be prepared by deprotecting an intermediate of general formula (VII)

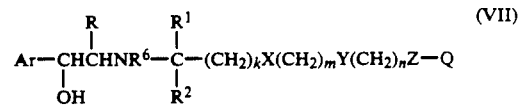

(VII)

wherein $R^6$ is a protecting group, and/or at least one of the hydroxy group(s) in Ar is protected, and/or the group Q contains a protecting group.

The protecting group may be any conventional protecting group as described for example in "Protective Groups in Organic Synthesis", by Theodora Greene (John Wiley and Sons Inc., 1981). Thus, for example, hydroxyl groups may be protected by arylmethyl groups such as benzyl, diphenylmethyl or triphenylmethyl, by acyl groups such as acetyl, or as tetrahydropyranyl derivatives. Examples of suitable amino protecting groups include arylmethyl groups such as benzyl, α-methylbenzyl, diphenylmethyl or triphenylmethyl, and acyl groups such as acetyl, trichloroacetyl or trifluoroacetyl.

The deprotection to yield a compound of general formula (I) may be effected using conventional techniques. Thus for example arylmethyl groups may be removed by hydrogenolysis in the presence of a metal catalyst (e.g. palladium on charcoal). Tetrahydropyranyl groups may be cleaved by hydrolysis under acidic conditions. Acyl groups may be removed by hydrolysis with an acid such as a mineral acid e.g. hydrochloric acid, or a base such as sodium hydroxide or potassium carbonate, and a group such as trichloroacetyl may be removed by reduction with, for example, zinc and acetic acid.

Intermediates of formula (VI) for use in the reduction process (2) in which $X^1$ is the group $>C=O$ may be prepared by reaction of a haloketone of formula (VIII)

$$Ar-COCHHal \quad \text{(VIII)}$$

(where Hal represents a halogen atom e.g. bromine) with an amine of formula (IX)

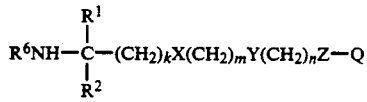

$$R^6NH-\underset{R^2}{\overset{R^1}{C}}-(CH_2)_kX(CH_2)_mY(CH_2)_nZ-Q \quad \text{(IX)}$$

(where $R^6$ is a hydrogen atom or a group convertible thereto by catalytic hydrogenation).

The reaction may be effected in a cold or hot solvent, for example tetrahydrofuran, tert-butyl methyl ether, dioxan, chloroform, dichloromethane, dimethylformamide, acetonitrile, a ketone such as butanone or methylisobutylketone, or an ester such as ethyl acetate, preferably in the presence of a base such as diisopropylethylamine, sodium carbonate or other acid scavenger such as propylene oxide.

Intermediates of general formula (VI) in which $X^1$ is the group $>C=O$ may be reduced to the corresponding intermediate in which $X^1$ is the group —CH(OH)— using for example a metal hydride such as sodium borohydride in a solvent e.g. ethanol, methanol and/or tetrahydrofuran.

Amines of formula (II) and haloketones of formula (VIII) are either known compounds or may be prepared by methods analogous to those described for the preparation of known compounds.

Intermediates of formula (III) may be prepared from the corresponding alcohols of formula (X) using methods capable of effecting the conversion.

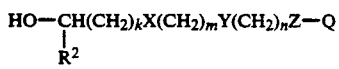

$$HO-\underset{R^2}{\overset{}{C}H}(CH_2)_kX(CH_2)_mY(CH_2)_nZ-Q \quad \text{(X)}$$

For example compounds of formula (III) where L represents a halogen atom may be prepared by reaction of the compounds of formula (X) with a halogenating agent such as a triphenylphosphine-tetrahalogenomethane adduct (conveniently formed in situ e.g. by the reaction of triphenylphosphine and carbon tetrabromide). The reaction may take place in the presence of a solvent such as a chlorinated hydrocarbon (e.g. dichloromethane) at a temperature range of 0°–30°.

Alcohols of formula (X) may be prepared by reacting a compound of formula (XI)

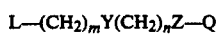

$$L-(CH_2)_mY(CH_2)_nZ-Q \quad \text{(XI)}$$

(where L is as defined above) with a compound of formula (XII)

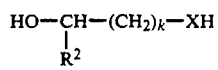

$$HO-\underset{R^2}{\overset{}{C}H}-(CH_2)_k-XH \quad \text{(XII)}$$

The reaction may take place optionally in a solvent such as an ether (e.g. tetrahydrofuran or 1,2-dimethoxyethane), an alcohol (e.g. methanol) or an amide (e.g. dimethylformamide) at a temperature up to the boiling point of the solvent. The reaction may be effected by first generating the anion of the compound of general formula (XII) by adding for example sodium, sodium hydride, potassium hydroxide or sodium hydroxide.

Compounds of formula (XI) may be prepared from the corresponding compounds of formula (XIII)

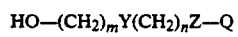

$$HO-(CH_2)_mY(CH_2)_nZ-Q \quad \text{(XIII)}$$

using methods capable of effecting the conversion. For example when L in general formula (XI) represents a hydrocarbylsulphonyloxy group (e.g. methanesulphonyloxy) such compounds may be prepared by reacting the compounds of formula (XIII) with methanesulphonyl chloride in the presence of a base (e.g. triethylamine). The reaction conveniently takes place in the presence of a solvent such as a halogenated hydrocarbon (e.g. dichloromethane) at a temperature ranging from 0°–25°.

Compounds of formula (XIII) in which Y represents an oxygen or sulphur atom may be prepared by reacting a compound of formula (XIV) with a compound of formula (XV)

$$L-(CH_2)_nZ-Q \quad \text{(XIV)}$$

$$HO(CH_2)_mYH \quad \text{(XV)}$$

under conditions as described for the preparation of compounds of formula (X) above.

Compounds of formula (XIV) are either known compounds or may be prepared from the corresponding alcohols as described for the preparation of compounds of formula (III) above.

Compounds of formulae (XII) and (XV) are either known compounds or may be prepared by methods analogous to those used for the preparation of known compounds.

In addition, suitable methods for preparing intermediates of formulae (III), (IV), (IX), (XI), (XIII) and (XIV) are described in UK Patent Specifications Nos. 2140800A and 2159151A and in the exemplification included hereinafter.

In the general processes described above, the compound of formula (I) obtained may be in the form of a salt, conveniently in the form of a physiologically acceptable salt. Where desired, such salts may be converted to the corresponding free bases using conventional methods.

Physiologically acceptable salts of the compounds of general formula (I) may be prepared by reacting a compound of general formula (I) with an appropriate acid or base in the presence of a suitable solvent such as acetonitrile, acetone, chloroform, ethyl acetate or an alcohol, e.g. methanol, ethanol or isopropanol.

Physiologically acceptable salts may also be prepared from other salts, including other physiologically acceptable salts, of the compounds of general formula (I), using conventional methods.

When a specific enantiomer of a compound of general formula (I) is required, this may be obtained by resolution of a corresponding racemate of a compound of general formula (I) using conventional methods.

Thus, in one example an appropriate optically active acid may be used to form salts with the racemate of a compound of general formula (I). The resulting mixture of isomeric salts may be separated for example by fractional crystallisation, into the diastereoisomeric salts from which the required enantiomer of a compound of general formula (I) may be isolated by conversion into the required free base.

Alternatively, enantiomers of a compound of general formula (I) may be synthesised from the appropriate optically active intermediates using any of the general processes described herein.

Specific diastereoisomers of a compound of formula (I) may be obtained by conventional methods for example, by synthesis from an appropriate asymmetric starting material using any of the processes described herein, or by conversion of a mixture of isomers of a compound of general formula (I) into appropriate diastereoisomeric derivatives e.g. salts which then can be separated by conventional means e.g. by fractional crystallisation.

The following examples illustrate the invention. Temperatures are in ° C. 'Dried' refers to drying using magnesium sulphate or sodium sulphate. Unless otherwise stated, thin layer chromatography (t.l.c.) was carried out on silica and flash column chromatography (FCC) on silica (Merck 9385) using one of the following solvent systems: A-ethyl acetate:methanol:triethylamine, B-toluene:ethanol:0.88 ammonia, C-toluene:ethanol:triethylamine. The following abbreviations are used: DMF-dimethylformamide, TAB-tetra-n-butylammonium hydrogen sulphate, DEA-N,N-diisopropylethylamine.

INTERMEDIATE 1

2-[2-[(6-Bromohexyl)oxy]ethyl]naphthalene

2-Naphthaleneethanol (3 g), 1,6-dibromohexane (8 ml), TAB (0.5 g) and sodium hydroxide (8 g) in 16 ml water) were stirred at room temperature under nitrogen for 26 h Water (80 ml) was added and the mixture extracted with diethyl ether ($3 \times 100$ ml). The combined extracts were washed with water (80 ml), brine (80 ml), dried and evaporated to give a colourless oil (13 g). The oil was purified by FCC eluting with cyclohexane (2l) and then cyclohexane-ethyl acetate (40:1) to give the title compound, (4.23 g), as a colourless oil, t.l.c. (cyclohexane:ethyl acetate; 5:1) Rf 0.45.

INTERMEDIATE 2

1-[2-[(6-Bromohexyl)oxy]ethyl]naphthalene

1-Naphthaleneethanol (3.00 g) and 1,6-dibromohexane (12.73 g) were treated according to the method of Intermediate 1. FCC eluting with cyclohexane followed by ethyl acetate-cyclohexane (1:20, then 1:4) gave the title compound (4.32 g) as a colourless oil.

Analysis Found: C,64.5; H,6.65; Br,23.75. $C_{16}H_{25}BrO$ requires C,64.5; H,6.9; Br,23.85%.

INTERMEDIATE 3

1-[[(5-Bromopentyl)oxy]methyl]naphthalene

1-Naphthalenemethanol (6.00 g) and 1,5-dibromopentane (11.5 ml) were treated according to the method of Intermediate 1. FCC eluting with ether-cyclohexane (1:49→2:48) gave the title compound as a colourless oil (8.41 g), t.l.c. (Cyclohexane-ether 19:1) Rf 0.22;

INTERMEDIATE 4

7-[(1-Naphthalenyl)methoxy]-2-heptanone

1-[[(5-Bromopentyl)oxy]methyl]naphthalene (9.96 g) in dry ether (40 ml) was added to magnesium turnings (0.94 g) and iodine (one small crystal) under nitrogen with stirring at a rate which maintained a gentle reflux. The mixture was stirred at reflux for 30 min, cooled to ambient temperature and added over 2.5 h to acetic anhydride (7.67 ml) in ether (15 ml) at $-78°$ under nitrogen with vigorous stirring. After 2 h at $-78°$, the mixture was allowed to warm to $-10°$ and treated with aqueous saturated ammonium chloride (50 ml). Ether (50 ml) was added, the aqueous layer was separated and the ethereal layer was washed with 1M-aqueous sodium hydroxide (100 ml). The combined aqueous washings were extracted with ether (100 ml) and this extract was combined with the ethereal layer above. The dried ethereal solution was evaporated and the residual oil purified FCC. Elution with ether-cyclohexane (1:4) gave, after Kugelrohr distillation, the title compound as a colourless oil (3.39 g), b.p. 190°/0.3 Torr (Kugelrohr).

INTERMEDIATE 5

N-[6-[[3-[6-Methoxy-2-naphthalenyl]-2-propynyl]oxy]hexyl]benzenemethanamine

Nitrogen was bubbled through a mixture of N-[6-[(2-propynyl)oxy]hexyl]benzenemethanamine (4.14 g), 2-bromo-6-methoxynaphthalene (4.0 g) and dicyclohexylamine (5.82 g) in acetonitrile (60 ml) for 15 min. Bis(-triphenylphosphine)palladium (II) chloride (120 mg) and copper (I) iodide (10 mg) were added and the mixture was stirred at reflux under nitrogen for 4 h, cooled, diluted with ether (100 ml), filtered and the filtrate evaporated in vacuo. Purification by FCC eluting with System B (90:10:1) gave the title compound as a brown oil (1.18 g), t.l.c. (System B 40:10:1) Rf 0.19.

INTERMEDIATE 6

(Z)-N-[5-[1-Hydroxy-2-[[6-[3-(6-methoxy-2-naphthalenyl)-2-propenyloxy]hexyl](phenylmethyl)amino]ethyl]-2-(phenylmethoxy)phenyl]methanesulphonamide A solution of N-[5-(bromoacetyl)-2-(phenylmethoxy)phenyl]methanesulphonamide (0.96 g), N-[6-[3-(6-methoxy-2-naphthalenyl)-2-propynyloxy]hexyl]benzenemethanamine (1.38 g) and DEA (0.47 g) in dichloromethane (22 ml) was stirred at room temperature under nitrogen for 22 h, diluted with water (100 ml) and extracted with dichloromethane ($2 \times 100$ ml). The combined organic extracts were dried and evaporated in vacuo to give an oil. The oil was dissolved in methanol (20 ml) and dichloromethane (20 ml) and sodium borohydride (0.25 g) were added portionwise to the solution at 0° C. under nitrogen. The solution was stirred at room temperature for 1 h, cooled to 0° C. and a further portion of sodium borohydride (0.1 g) added. The solution was stirred at room temperature for 30 min and then carefully diluted with water (10 ml) and evaporated in vacuo. The residue was partitioned between dichloromethane (100 ml) and water (100 ml). The aqueous phase was re-extracted with dichloromethane (100 ml) and the combined organic fractions dried and evaporated in vacuo to give an oil. Purification by FCC eluting with System C (100:2:1) gave the title compound as a colourless oil (0.77 g), t.l.c. (System C 98:2:1) Rf 0.23.

INTERMEDIATE 7

4-Amino-3,5-dichloro-α-[[[6-[[3-[6-methoxy-2-naphthalenyl]-2-propynyl]oxy]hexyl](phenylmethyl)amino]methyl]benzenemethanol A solution of 1-(4-amino-3,5-dichloro)-2-bromoethanone (0.78 g), N-[6-[[3-[6-methoxy-2-naphthalenyl]-2-propynyl]oxy]hexyl]benzenemethanamine (1.1 g) and DEA (0.39 g) in tetrahydrofuran (25 ml) was stirred under nitrogen for 20 h. The mixture was filtered and the filtrate evaporated in vacuo to give an oil. The oil was dissolved in methanol (20 ml) and dichloromethane (30 ml) and sodium borohydride (0.28 g) added portionwise to the solution at 0° C. under nitrogen. The solution was stirred at room temperature for 2 h, cooled to 0° C. and a further portion of sodium borohydride (0.14 g) added. The solution was then stirred at room temperature for 1 h, carefully diluted with water (10 ml) and evaporated in vacuo. The residue was partitioned between ethyl acetate (100 ml), water (100 ml), the aqueous phase was re-extracted with ethyl acetate (100 ml) and the combined organic fractions dried and evaporated in vacuo to give an oil. Purification by FCC eluting with System C (100:1:1) gave the title compound as a colourless oil (1.18 g), t.l.c. (System C 98:2:1) Rf 0.53

INTERMEDIATE 8

4-[(2-Naphthalenyl)oxy]butanol

A mixture of 2-[(4-bromobutyl)oxy]naphthalene (5.5 g), sodium acetate (13.1 g), trioctylpropylammonium chloride (1.21 g) and water (19 ml) was stirred at ca 100° for 2 h. 2N sodium hydroxide solution (32 ml) and ethanol (32 ml) were added to the cooled mixture which was stirred for a further 10 min at room temperature. The ethanol was evaporated in vacuo and the residue diluted with brine (150 ml) and extracted with ether (2×100 ml), which was dried and evaporated in vacuo to give a white solid. The solid was dissolved in ether and purified by FCC eluting with hexane-ether (2:1→1:2) to give the title compound as a white solid (1.36 g), m.p. 66.5°-67.5°.

INTERMEDIATE 9

2-[4-[(6-Bromohexyl)oxy]butoxy]naphthalene

A mixture of 4-[(2-naphthalenyl)oxy]butanol (2.4 g), 1,6-dibromohexane (5.3 ml), TAB (1 g) and 50% sodium hydroxide solution (24 ml) was stirred at room temperature for 19 h. The mixture was diluted with water (100 ml) and extracted with ether (2×150 ml). The combined organic fractions were dried and evaporated in vacuo to give an oil. Purification by FCC eluting with hexane followed by hexane-ether (19:1→8:1) gave the title compound as a colourless oil, (2.34 g), t.l.c. (ether-hexane 1:1) Rf 0.85.

INTERMEDIATE 10

N-[6-[4-[(2-Naphthalenyl)oxy]butoxy]hexyl]benzenemethanamine

2-[4-[(6-Bromohexyl)oxy]butoxy]naphthalene (2.25 g) and benzylamine (3.88 g) were stirred under nitrogen at ca. 125° for 2 h. The solution was diluted with 8% sodium bicarbonate (100 ml) and extracted with diethyl ether (2×100 ml), dried and evaporated in vacuo to give an oil. Purification by FCC eluting with System C (98:2:1) gave the title compound as a yellow oil (2.3 g), t.l.c. (System C 40:10:1) Rf 0.71.

INTERMEDIATE 11

2-[[2-[(6-Bromohexyl)oxy]ethyl]thio]naphthalene

A mixture of 1,6-dibromohexane (9 ml), 50% w/v sodium hydroxide (40 ml), 2-(2-naphthalenyl)thioethanol (4 g), TAB (0.8 g) and hexane (30 ml) was stirred vigorously at 20°, under nitrogen for 4 h. Water (100 ml) and ether (100 ml) were added and the mixture was further extracted with ether (100, 2×50 ml). The combined, dried ether extracts were evaporated in vacuo to give a yellow oil. Purification by FCC eluting with light petroleum (b.p. 60°-80°):ether (30:1→1:1) gave the title compound as a white crystalline solid (5.7 g), m.p. 38°-40° (softens 36°).

EXAMPLE 1

4-Hydroxy-α¹-[[[6-[2-(2-naphthalenyl)ethoxy]hexyl]amino]methyl]-1,3-benzenedimethanol α¹-(Aminomethyl)-4-hydroxy-1,3-benzenedimethanol (1.31 g), 2-[2-[(6-bromohexyl)oxy]ethyl]naphthalene (2 g) and DEA (0.83 ml) in DMF (dried over type 4 Å sieves, 20 ml) were stirred at 100° under nitrogen for 2 h. The cooled mixture was poured into aqueous saturated sodium bicarbonate (80 ml) and extracted with ethyl acetate (3×100 ml). The combined extracts were washed (water, 100 ml), dried and evaporated to give a yellow tacky solid (3.5 g). This solid was adsorbed onto silica (Merck 7734, 2 g) from methanol and the resultant silica gel plug was applied to an FCC column. Elution with System A (89:10:1) gave a white solid (0.95 g), which crystallised from ethyl acetate (20 ml) to give the title compound (0.32 g) as a white solid, m.p. 112°-114°.

Analysis Found: C,73.3; H,8.2; N,3.1.
C₂/H₃₅NO₄.0.2H₂O requires C,73.5; H,8.1; N,3.2%.
Water analysis, 0.2 mole water

EXAMPLE 2

4-Hydroxy-α¹-[[[6-[2-(1-naphthalenyl)ethoxy]hexyl]amino]methyl]-1,3-benzenedimethanol A mixture of α¹-(aminomethyl)-4-hydroxy-1,3-benzenedimethanol (0.75 g), 1-[2-[(6-bromohexyl)oxy]ethyl]naphthalene (1.00 g), DEA (0.85 ml) in DMF (6.5 ml) was heated at 80° for 2 h. The clear brown solution was diluted with water (65 ml), acidified to pH4 with 2N hydrochloric acid and then basified to pH8 with solid potassium bicarbonate. The mixture was extracted with ethyl acetate (2×65 ml) and the combined extracts were washed with water (65 ml) and brine (30 ml). The dried extracts were evaporated, the residue dissolved in ethyl acetate-methanol (1:1) and absorbed onto silica (Merck 7734, 5.00 g). The silica gel plug was applied to an FCC column and elution with System A (90:10:1) gave the title compound (0.22 g) as a white solid m.p. 105°-107°.

Analysis Found: C,73.1; H,7.85; N,3.1.
C₂/H₃₅NO₄ 0.33H₂O requires C,73.1; H,8.1; N,3.1%.

EXAMPLE 3

4-Hydroxy-α¹-[[[1-methyl-6-[[(1-naphthalenyl)methyl]oxy]hexyl]amino]methyl]-1,3-benzenedimethanol 7-[(1-naphthalenyl)methoxy]-2-heptanone (1.00 g) and α¹-[[bis(phenyl methyl)amino]methyl]-4-hydroxy-1,3-benzenedimethanol (1.34 g) in ethanol (40 ml) were hydrogenated over pre-reduced 10% palladium oxide-on-carbon (0.2 g) and 5% platinum oxide-on-carbon (0.2 g) at room temperature and pressure. The catalyst was removed (hyflo) and the solution evaporated. The residual oil was purified by FCC, eluting with System A (94:5:1) to give a white solid (704 mg). The white solid was further purified by repeating the chromatography procedure to give the title compound as a white solid (469 mg) m.p. 99°-101°

Analysis Found: C,73.7;H,8.5;N,3.15. $C_2/H_{35}NO_4$ requires C,74.1;H,8.05;N,3.2%.

EXAMPLE 4

N-[2-Hydroxy-5-[1-hydroxy-2-[[6-[3-(6-methoxy-2-naphthalenyl)propoxy]hexyl]amino]ethyl]phenyl]methanesulphonamide A solution of Z-N-[5-[1-hydroxy-2-[6-[3-(6-methoxy-2-naphthalenyl)-2-propenyloxy]hexyl](phenylmethyl)amino]methyl]benzenemethanol (0.73 g) in absolute ethanol (30 ml) was hydrogenated over pre-reduced 10% palladium on charcoal catalyst (0.4 g) in absolute ethanol (10 ml). The mixture was filtered through hyflo and evaporated in vacuo. The resultant solid was dissolved in dichloromethane (50 ml) and washed with 8% sodium bicarbonate (50 ml). The aqueous phase was re-extracted with dichloromethane (50 ml) and the combined organic extracts dried and evaporated in vacuo to give a solid. Trituration with diethyl ether gave the title compound as an off-white solid (0.25 g), m.p. 87°-89°.

Analysis Found: C,63.2; H,7.1; N,5.1. $C_{29}H_{40}N_2O_6S.0.25H_2O$ requires C,63.4; H,7.4; N,5.1%.

EXAMPLE 5

4-Amino-3,5-dichloro-α-[[[6-[3-(6-methoxy-2-naphthalenyl)propoxy]hexyl]amino]methyl]benzenemethanol A solution of 4-amino-3,5-dichloro-α-[[[6-[[3-[6-methoxy-2-naphthalenyl]-2-propynyl]oxy]hexyl](phenylmethyl)amino]methyl]benzenemethanol (1.11 g) in absolute ethanol (50 ml) was hydrogenated over pre-reduced 10% palladium on charcoal catalyst (0.4 g) in absolute ethanol (10 ml) containing hydrochloric acid (1:9 conc. hydrochloric acid/ethanol, 1.67 ml). The mixture was filtered through hyflo and evaporated in vacuo to give an oil. The oil was partitioned between dichloromethane (150 ml) and 8% sodium bicarbonate (100 ml). The aqueous phase was re-extracted with dichloromethane (100 ml) and the combined organic extracts dried and evaporated in vacuo to give an oil. Purification by FCC eluting with System C (95:5:1) gave the title compound as a white solid (513 mg), m.p. 102.5°-103.5°.

Analysis Found: C,64.5;H,7.5;N,5.3;Cl,13.9. $C_{28}H_{36}Cl_2N_2O_3$ requires C,64.7; H,7.0; N,5.4; Cl,13.6%

EXAMPLE 6

5-[1-Hydroxy-2-[[6-[(2-naphthalenyl)ethoxy]hexyl]amino]ethyl]-1,3-benzenediol,4,4'-methylenebis[3-hydroxy-2-naphthalenecarboxylate](2:1) salt A mixture of 5-(2-amino-1-hydroxyethyl)-1,3-benzenediol (1.02 g), 2-[3-[(6-bromohexyl)oxy]ethyl]naphthalene (1.34 g) and DEA (1.74 ml) in DMF (25 ml) was heated at 100° for 3 h under nitrogen. The solvent was removed in vacuo and the residue purified by FCC eluting with System B (80:20:1) to give the base as a solid pink glass (0.8 g).

A mixture of the base (0.4 g) and 4,4'-methylenebis[3-hydroxy-2-naphthalenecarboxylic acid] (0.18 g) in methanol (30 ml) was heated under reflux for 30 min. The methanol was removed in vacuo and the residue triturated under ether (20 ml) to give the title compound as an off-white solid (0.52 g), m.p. 105°-110° (softens 100°).

Analysis Found: C,70.2; H,6.9; N,2.1. $(C_{26}H_{33}NO_4)_2$ $C_2H_{16}O_6.2.5H_2O$ requires C,70.35; H,6.85; N,2.2%.

EXAMPLE 7

N-[2-Hydroxy-5-[1-hydroxy-2-[[6-[4-[(2-naphthalenyl)oxy]butoxy]hexyl]amino]ethyl]phenyl]methanesulphonamide A solution of N-[5-(bromoacetyl)-2-(phenylmethoxy)phenyl]methanesulphonamide (1.96 g), N-[6-[4-[(2-naphthalenyl)oxy]butoxy]hexyl]benzenemethanamine (2.0 g) and DEA (0.96 g) in dichloromethane (45 ml) was stirred under nitrogen at room temperature for 22 h. The mixture was treated with water (100 ml) and extracted with dichloromethane (2×150 ml). The combined organic extracts were dried and evaporated in vacuo to give an oil which was dissolved in methanol (30 ml) and dichloromethane (20 ml) and cooled to 0°-5° C. under nitrogen. Sodium borohydride (0.50 g) was added portionwise and the solution stirred at room temperature for 30 min, then carefully diluted with water (20 ml). The solvent was evaporated in vacuo, the residue partitioned between water (100 ml) and dichloromethane (150 ml) and the aqueous phase re-extracted with dichloromethane (150 ml), the combined organic extracts being dried and evaporated in vacuo to give an oil which was purified by FCC eluting with System C (95:5:1). A solution of the oil (3.41 g) in absolute ethanol (60 ml) was hydrogenated over pre-reduced 10% palladium on charcoal catalyst (50% aqueous paste, 1.5 g) in absolute ethanol (10 ml) for 4.5 h. The mixture was filtered through hyflo and evaporated in vacuo to give an oil which was purified by FCC eluting with System B (40:10:1) to give a cream solid. Trituration with diethyl ether gave the title compound as a white solid (1.23 g), m.p. 99.5°-100.5°.

Analysis Found: C,64.1; H,7.3; N,5.2. $C_{29}H_{40}N_2O_6S$ requires C,63.9; H,7.4; N,5.1%.

EXAMPLE 8

N-[2-Hydroxy-5-[1-hydroxy-2-[[6-[4-[(2-naphthalenyl)oxy]butoxy]hexyl]amino]ethyl]phenyl]methanesulphonamide, 4,4'-methylenebis-[3-hydroxy-2-naphthalenecarboxylate] salt (2:1)

A solution of N-[2-hydroxy-5-[2-hydroxy-2-[[6-[4-[(2-naphthalenyl) oxy]butoxy]hexyl]amino]ethyl]phenyl]methanesulphonamide (449 mg) in methanol (17 ml) and 4,4'-methylenebis[3-hydroxy-2-naphthalenecarboxylic acid] (160 mg), was heated at reflux for 1 h, cooled, filtered and the filtrate evaporated in vacuo. The residue was triturated with dry ether to afford the title compound as an off-white foam (413 mg), m.p. 100°-106°.

Assay Found: C,65.0; H,6.6; N,3.7; S,4.2. $C_{29}H_{40}N_2O_6S.0.5C_{23}H_{16}O_6.0.5H_2O$ requires C,65.0; H,6.6; N,3.75; S,4.3%.

EXAMPLE 9

4-Hydroxy-$\alpha^1$-[[[6-[2-[(2-naphthalenyl)thio]ethoxy]hexyl]amino]methyl]-1,3-benzenedimethanol A solution of $\alpha^1$-(aminomethyl)-4-hydroxy-1,3-benzenedimethanol (1.0 g), 2-[[2-[(6-bromohexyl)oxy]ethyl]thio]naphthalene (1.01 g) and DEA (0.52 g) in dry DMF (30 ml) was stirred at 100° under nitrogen for 4 h. The solvent was evaporated and the residue purified by FCC eluting with System B (39:10:1) to give a pale brown solid (0.76 g). Trituration under ether (2×50 ml) gave the title compound as a cream coloured solid (0.39 g.), m.p. 101°–2°.

Analysis Found: C,68.9; H,7.6; N,3.0; S,6.6. $C_2/H_{35}NO_4S$ requires C,69.05; H,7.5; N,3.0; S,6.8%.

The following are examples of suitable formulations of compounds of the invention. The term 'active ingredient' is used herein to represent a compound of the invention.

TABLETS

Direct Compression

|  | mg/tablet |
| --- | --- |
| Active ingredient | 2.0 |
| Microcrystalline cellulose USP | 196.5 |
| Magnesium Stearate BP | 1.5 |
| Compression weight | 200.0 |

The active ingredient is sieved through a suitable sieve, blended with the excipients and compressed using 7 mm diameter punches.

Tablets of other strengths may be prepared by altering the ratio of active ingredient to microcrystalline cellulose or the compression weight and using punches to suit.

The tablets may be film coated with suitable film forming materials, such as hydroxypropylmethylcellulose, using standard techniques. Alternatively, the tablets may be sugar coated.

METERED DOSE PRESSURISED AEROSOL

Suspension Aerosol

|  | mg/metered dose | Per can |
| --- | --- | --- |
| Active ingredient micronised | 0.100 | 26.40 mg |
| Oleic Acid BP | 0.100 | 2.64 mg |
| Trichlorofluoromethane BP | 23.64 | 5.67 g |
| Dichlorodifluoromethane BP | 61.25 | 14.70 g |

The active ingredient is micronised in a fluid energy mill to a fine particle size range. The oleic acid is mixed with the trichlorofluoromethane at a temperature of 10°–15° C. and the micronised drug is mixed into the solution with a high shear mixer. The suspension is metered into aluminium aerosol cans and suitable metering valves delivering 85 mg of suspension are crimped onto the cans and the dichlorodifluoromethane is pressure filled into the cans through the valves.

INHALATION CARTRIDGES

|  | mg/cartridge |
| --- | --- |
| Active ingredient micronised | 0.200 |
| Lactose BP to | 25.0 |

The active ingredient is micronised in a fluid energy mill to a fine particle size range prior to blending with normal tabletting grade lactose in a high energy mixer. The power blend is filled into No. 3 hard gelatin capsules on a suitable encapsulating machine. The contents in the cartridges are administered using a powder inhaler such as the Glaxo Rotahaler.

We claim:

1. A method of treating a patient suffering from an inflammatory or allergic skin disease, which method comprises administering to said patient an effective amount to alleviate said condition of at least one compound of the formula.

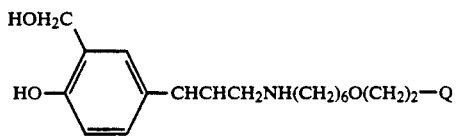

or a physiologically acceptable salt or solvate thereof, wherein Q represents a 1- or 2- naphthalenyl group.

2. A method according to claim 1 wherein the compound comprises 4-hydroxy-$\alpha^1$-[[[6-[2-(2-(1-naphthalenyl)ethoxy]hexyl]amino]methyl]-1,3-benzenedimethanol or a physiologically acceptable salt or solvate thereof.

3. A method according to claim 1 where the compound comprises 4-hydroxy-$\alpha^1$-[[[6-[2-(2-naphthalenyl)ethoxy]hexyl]amino]methyl]-1,3-benzenedimethanol or a physiologically acceptable salt or solvate thereof.

* * * * *